US006926886B2

(12) United States Patent
Lin et al.

(10) Patent No.: US 6,926,886 B2
(45) Date of Patent: Aug. 9, 2005

(54) COMPOSITIONS FOR DARKENING THE SKIN AND/OR HAIR

(75) Inventors: Connie Baozhen Lin, Belle Mead, NJ (US); Jane Zhenyi Wu, Shanghai (CN)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 117 days.

(21) Appl. No.: 10/285,108

(22) Filed: Oct. 31, 2002

(65) Prior Publication Data

US 2004/0091449 A1 May 13, 2004

(51) Int. Cl.$^7$ .............................. A61K 7/42; A61K 7/44; A61K 7/00; A61K 35/78
(52) U.S. Cl. .......................... 424/59; 424/60; 424/400; 424/401; 424/725
(58) Field of Search ........................... 424/59, 60, 400, 424/401, 725

(56) References Cited

U.S. PATENT DOCUMENTS

| | | | |
|---|---|---|---|
| 4,129,644 A | 12/1978 | Klopissis et al. | |
| 4,987,150 A | 1/1991 | Kurono et al. | |
| 5,013,497 A | 5/1991 | Yiounas et al. | |
| 5,216,116 A | 6/1993 | Pawelek | |
| 5,218,079 A | 6/1993 | Pawelek et al. | |
| 5,225,435 A | 7/1993 | Pawelek et al. | |
| 5,227,459 A | 7/1993 | Pawelek et al. | |
| 5,260,065 A | 11/1993 | Mathur et al. | |
| 5,384,116 A | 1/1995 | Pawelek et al. | |
| 5,618,519 A | 4/1997 | Pawelek et al. | |
| 5,744,125 A | 4/1998 | Pawelek et al. | |
| 6,153,208 A | * 11/2000 | McAtee et al. | 424/402 |
| 6,551,581 B1 | * 4/2003 | Mahalingam et al. | 424/59 |
| 6,620,419 B1 | 9/2003 | Lintner | |

FOREIGN PATENT DOCUMENTS

| | | |
|---|---|---|
| EP | 0273202 B1 | 7/1988 |
| EP | 0941103 B1 | 1/2002 |
| JP | 0405237 | 7/1993 |
| JP | 6025663 | 2/1994 |
| JP | 7010733 | 1/1995 |
| JP | 7138173 | 5/1995 |
| JP | 2000212059 | 8/2000 |
| JP | 2000281528 | 10/2000 |
| WO | WO98/19688 A1 | 5/1998 |
| WO | WO00/15188 A1 | 3/2000 |

OTHER PUBLICATIONS

John A. Wenninger, G.N.McEwen, Jr., International Cosmetic Ingredient Dictionary and Handbook, 7$^{th}$ Edition, 1997, The Cosmetic, Toiletry, and Fragrance Association, pp. 1626, 1654–1661, 1673–1686, 1693–1697.

Theory and Practice of Histo–Technology, St. Louis:CV Mosby, 1980, pp. 223–277.

Product data sheets for Cuivridone by Barnet Products Corp. dated Nov. 17, 1999.

International Search Report dated May 26, 2004, for corresponding application PCT/US03/34384.

* cited by examiner

Primary Examiner—Shelley A. Dodson
(74) Attorney, Agent, or Firm—William E. McGowan

(57) ABSTRACT

The present invention relates to a composition containing rhubarb extract and the use thereof in darkening the skin and/or hair.

14 Claims, No Drawings

COMPOSITIONS FOR DARKENING THE SKIN AND/OR HAIR

FIELD OF THE INVENTION

The present invention relates to the use of rhubarb extract in darkening the skin and/or hair.

BACKGROUND OF THE INVENTION

The darkening of skin color is a concern for many individuals. Most people obtain darker skin through exposure to UV light (e.g., suntanning or UV lamps). Production of melanin and the type of melanin when stimulated by UV are genetically determined. UV exposure, however, results in accelerated skin aging and increased incidence of skin cancer. The ability to generate a tanned appearance without incurring photodamage, thus, is important to many individuals. Accordingly, alternative methods for "sunless tanning" have evolved.

One method is the use of products containing dihydroxy acetone (DHA). Some of these products, however, produce color that is too orange and unnatural to the user. Moreover, the DHA-produced skin color only minimally protects the user from UV irradiation. Products containing beta-carotene, cantaxanthin and lycopene have also been used to darken the skin. These products, however, have no effect at all on melanogenesis and usually result in unnatural and uneven distributed skin color by saturating and staining the fat layers just below the skin. In addition, these products do not provide any sun-protection as compared to naturally tanned skin. Melanotan and MelanX are synthetic hormone drugs that mimic the action of melanocyte-stimulating hormone (MSH) and are used to darken the skin only when administered by injection, not orally or topically. Psoralens, on the other hand, work by making the skin hypersensitive to the sun and therefore melanin production is accelerated. They do not make the skin darker without exposure to UV, and that exposure must be carefully regulated to minimize the serious risk for skin cancer. Psoralens in conjunction with medical grade UV lamps are an accepted treatment for people afflicted with vitiligo and psoriasis, but are not recommended for patients with fair skins. Thus, a product is desired that would enhance the body's natural pigment content, resulting in a desired skin color and enhanced photo-protection without the need of UV exposure.

Rhubarb is one of the oldest and well-known Chinese herbal medicines. Rhubarb root has traditionally been used as a laxative, antiphlogistic, and haemostatic in the treatment of constipation, jaundice, gastrointestinal hemorrhage, menstrual disorders, conjunctivitis, traumatic injuries, superficial sores and ulcers. It has also been applied externally for thermal burns. Rhubarb has been reported for the treatment of dermatosis such as atopic dermatitis (see Japanese Patent Nos. 07138173 and 07010733), for being an antioxidant (Japanese Patent Nos. 06025663 and 04005237), and for the cosmetic applications such as melanin formation inhibitor (Japanese Patent No. 2000281528) and improving skin roughness (Japanese Patent No. 2000212059). It has also been reported for the treatment of diabetes (European Patent No. 0941103 and PCT Patent Application No. WO9819688) and for inhibiting binding of 5-dihydro-testosterone with androgen receptors (U.S. Pat. No. 4,987,150).

The present inventors have now unexpectedly discovered that rhubarb is effective for darkening the skin and/or hair.

SUMMARY OF THE INVENTION

In one aspect, the present invention relates to a composition for darkening the skin or hair containing a safe and effective amount of a rhubarb extract and a cosmetically acceptable carrier. In another aspect, the present invention relates to a method of darkening the skin or hair including topically applying to the skin or hair a composition containing a safe and effective amount of a rhubarb extract. In another aspect, the present invention relates to a product including: (a) a composition for darkening the skin or hair, wherein such composition contains a safe and effective amount of a rhubarb extract; and (b) instructions directing the user to apply the composition to the skin or hair to darken the such skin or hair.

In still another aspect, the present invention relates to a method of promoting a product containing a composition where such composition contains a safe and effective amount of a rhubarb, wherein such method includes directing the user to apply such composition to the skin or hair to darken the skin or hair.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

What is meant by "darkening the skin or hair" is darkening the appearance of the skin or hair, including, but not limited to, darkening the skin to either achieve a "sun tan" effect or to cover the light areas of the skin (e.g., as a result of a scar or a disease such as vitiligo) or darkening natural hair color or restoring discolored hair due to aging (e.g., gray or white hair) or external aggressions (e.g., excess exposure to sun or chlorine).

What is meant by a "product" is a product in finished packaged form. In one embodiment, the package is a container such as a plastic, metal or glass tube or jar containing the composition. The product may further contain additional packaging such as a plastic or cardboard box for storing such container. In one embodiment, the product contains instructions directing the user to apply the composition to the skin or hair to darken the skin (e.g., to tan the skin), even skin tone (e.g., to darken light areas of the skin or to treat or prevent mottled hyperpigmentation), or darken the hair (e.g., to darken light brown, blonde, gray or white hairs). Such instructions may be printed on the container, label insert, or on any additional packaging.

What is meant by "promoting" is promoting, advertising, or marketing. Examples of promoting include, but are not limited to, written, visual, or verbal statements made on the product or in stores, magazines, newspaper, radio, television, internet, and the like. Examples of such statements include, but are not limited to, "evens skin tone," "darkens the skin," "evens hair color," "darkens the hair," "restore the original hair color," "treats and/or prevents gray hair," "prevents, reduces, and/or treats mottled hyperpigmentation," "tans the skin," or "sunless tan."

As used herein, "topically applying" means directly laying on or spreading on outer skin, scalp, or hair, e.g., by use of the hands or an applicator such as a wipe, roller, or spray.

As used herein, "cosmetically-acceptable" means that the ingredients which the term describes are suitable for use in contact with tissues (e.g., the skin or hair) without undue toxicity, incompatibility, instability, irritation, allergic response, and the like.

As used herein, "safe and effective amount" means an amount of the copper PCA or ester thereof, tyrosine or a salt or ester thereof, or DOPA or a salt or ester thereof or of the composition sufficient to induce a darkening of the skin or hair, but low enough to avoid serious side effects. The safe and effective amount of the compounds or composition will vary with the area being treated, the age and skin type of the end user, the duration and nature of the treatment, the specific extract, ingredient, or composition employed, the particular cosmetically-acceptable carrier utilized, and like factors.

Rhubarb Extract

What is meant by a "rhubarb extract" is a blend of compounds isolated from a plant from the genus Rheum, which includes, but is not limited to, the plant *R. rhubarbarum*. In one embodiment, the compounds are isolated from the root of the plant. Such compounds may be isolated from a part(s) of the plant (e.g., the seed, root, rhizome, fruit and/or leaf of the plant) by physically removing a piece of such plant, such as grinding a root of the plant. Such compounds may also be isolated from the plant by using extraction procedures well known in the art (e.g., the use of organic solvents such as lower $C_1$–$C_8$ alcohols, $C_1$–$C_8$ alkyl polyols, $C_1$–$C_8$ alkyl ketones, $C_1$–$C_8$ alkyl ethers, acetic acid $C_1$–$C_8$ alkyl esters, and chloroform, and/or inorganic solvents such as water, inorganic acids such as hydrochloric acid, and inorganic bases such as sodium hydroxide). In one embodiment, the rhubarb extract contains only hydrophilic compounds (e.g., isolated by using a hydrophilic solvent, such as water or ethanol). In one embodiment, the rhubarb extract is an aqueous extract from the root.

The amount of the rhubarb extract present in the composition will depend on the type of extract used. The extract typically will be present in the composition in an amount from about 0.001% to about 20% by weight, in particular in an amount from about 0.01% to about 5% by weight.

Pigment

In one embodiment, the composition of the present invention further contains at least one pigment. What is meant by a "pigment" is a compound(s) that can be taken up by epidermal cells, resulting in visually darker look to the skin or hair. Examples of such pigments include, but not limiting to, melanin and melanin derivatives (e.g, both melanin polymers and lower molecular weight water-soluble melanin derivatives); extracts from natural sources containing pigments (e.g., brown pigments from plants from the Hedychium genus or Bearberry genus or yellow, orange and red pigments, from plants containing carotenoids or canthaxanthins); or synthetic chemicals such as compounds containing copper (e.g., copper salts such as $CuCl_2$) or synthetic carotenoids or canthaxantins. Examples of synthetic melanin derivatives are disclosed in U.S. Pat. Nos. 5,618,519, 5,384,116, and 5,227,459. Examples of soluble melanin derivatives are disclosed in U.S. Pat. Nos. 5,744,125, 5,225,435, 5,218,079, and 5,216,116. Examples of commercially available soluble melanin derivatives include Melasyn-100™ from San-mar laboratories, Inc. (Elmsford, N.Y.) and MelanZe™ from Zylepsis (Ashford, Kent, United Kingdom).

The amount of pigment(s) present in the composition will depend on the type of pigment(s) used. The pigments typically will be present in the composition in an amount from about 0.001% to about 20% by weight, in particular in an amount from about 0.005% to about 5% by weight.

Dihydroxy Acetone and Lawsone

In one embodiment, the composition of the present invention further contains dihydroxyacetone and/or lawsone. These agents will typically be present in the composition in an amount from about 0.001% to about 10% by weight, in particular in an amount from about 1% to about 7% by weight. In one embodiment, the composition of the present invention contains both dihydroxyacetone and at least one pigment.

Peptides

In one embodiment, the composition of the present invention further contains a peptide of the Formula I Formula I

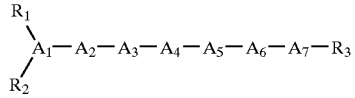

wherein:

$A_1$ is Ser or 2,3-diaP, or is absent;

$A_2$ is Val, Leu, Ile, or Cha;

$A_3$ is Val, Leu, Ile, or Cha;

$A_4$ is Gly or Ala;

$A_5$ is Lys, Arg, or Har;

$A_6$ is Val, Leu, Ile, or Cha, or is absent;

$A_7$ is Asp or Glu, or is absent; provided, $A_7$ is absent if $A_6$ is absent;

each $R_1$ and $R_2$, independently, is H, $C_{1-12}$ alkyl, $C_{7-10}$ phenylalkyl, or C(=O)$E_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is C(=O)$E_1$, the other must be H; and $R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, or $C_{11-20}$ naphthylalkylamino;

or a cosmetically acceptable salt thereof.

In one embodiment, $R_1$ and $R_2$, which are bound to the N-terminus of the peptide, are both H. In another embodiment, $R_1$ is H and $R_2$ is C(=O)$E_1$ (e.g., palmitoyl, oleatoyl, or stearatoyl).

Examples of peptides of the present invention include, but are not limited to, to $H_2$-Leu-Ile-Gly-Arg-$NH_2$ (Peptide 1, SEQ ID NO:1), $H_2$-Leu-Ile-Gly-Arg-Leu-$NH_2$ (Peptide 2, SEQ ID NO:2), $H_2$-Leu-Ile-Gly-Lys-$NH_2$ (Peptide 3, SEQ ID NO:3), $H_2$-Ser-Leu-Ile-Gly-Lys-$NH_2$ (Peptide 4, SEQ ID NO:4), $H_2$-Leu-Ile-Gly-Arg-OH (SEQ ID NO:5), $H_2$-Leu-Ile-Gly-Arg-Leu-OH (SEQ ID NO:6), $H_2$-Leu-Ile-Gly-Lys-OH (SEQ ID NO:7), $H_2$-Ser-Leu-Ile-Gly-Lys-OH (SEQ ID NO:8), Palmitoyl-Leu-Ile-Gly-Arg-$NH_2$ (SEQ ID NO:9), Palmitoyl-Leu-Ile-Gly-Arg-Leu-$NH_2$ (SEQ ID NO:10), Palmitoyl-Leu-Ile-Gly-Lys-$NH_2$ (SEQ ID NO:11), Palmitoyl-Ser-Leu-Ile-Gly-Lys-$NH_2$ (SEQ ID NO:12), Palmitoyl-Leu-Ile-Gly-Arg-OH (SEQ ID NO:13), Palmitoyl-Leu-Ile-Gly-Arg-Leu-OH (SEQ ID NO:14), Palmitoyl-Leu-Ile-Gly-Lys-OH (SEQ ID NO:15), Palmitoyl-Ser-Leu-Ile-Gly-Lys-OH (SEQ ID NO:16), Stearatoyl-Leu-Ile-Gly-Arg-$NH_2$ (SEQ ID NO:17), Stearatoyl-Leu-Ile-Gly-Arg-Leu-$NH_2$ (SEQ ID NO:18), Stearatoyl-Leu-Ile-Gly-Lys-$NH_2$ (SEQ ID NO:19), Stearatoyl-Ser-Leu-Ile-Gly-Lys-NH$_2$ (SEQ ID NO:20),
Stearatoyl-Leu-Ile-Gly-Arg-OH (SEQ ID NO:21),
Stearatoyl-Leu-Ile-Gly-Arg-Leu-OH (SEQ ID NO:22),
Stearatoyl-Leu-Ile-Gly-Lys-OH (SEQ ID NO:23),
Stearatoyl-Ser-Leu-Ile-Gly-Lys-OH (SEQ ID NO:24),
H$_2$-Ser-Leu-Ile-Gly-Arg-Leu-NH$_2$ (SEQ.ID.No.25),
H$_2$-Ser-Leu-Ile-Gly-Arg-Leu-OH (SEQ.ID.No.26),
Palmitoyl-Ser-Leu-Ile-Gly-Arg-Leu-NH$_2$ (SEQ.ID.No.27),
Palmitoyl-Ser-Leu-Ile-Gly-Arg-Leu-OH (SEQ.ID.No.28),
Stearatoyl-Ser-Leu-Ile-Gly-Arg-Leu-NH$_2$ (SEQ.ID.No.29), and Stearatoyl-Ser-Leu-Ile-Gly-Arg-Leu-OH (SEQ.ID.No.30), or a cosmetically-acceptable salt thereof.

The symbol A$_1$, A$_2$, or the like used herein (e.g., in Figure 1) stands for the residue of an alpha-amino acid. Such symbols represent the general structure, —NH—CH(X)—CO— or =N—CH(X)—CO— when it is at the N-terminus or —NH—CH(X)—CO— when it is not at the N-terminus, where X denotes the side chain (or identifying group) of the alpha-amino acid, e.g., X is —CH(CH$_3$)$_2$ for Val. Note that the N-terminus is at the left and the C-terminus at the right in accordance with the conventional representation of a polypeptide chain. R$_1$ and R$_2$ are both bound to the free nitrogen atom N-terminal amino acid (e.g., A$_1$ or A$_2$) and the R$_3$ is bound to the free carboxy group of the C-terminal amino acid (e.g., A$_5$, A$_6$, or A$_7$).

"Cha" herein refers to cyclohexylalanine, "2,3-diaP" refers to 2,3-diaminoproprionic acid, and "Har" refers to homoarginine. Furthermore, where the amino acid residue is optically active, it is the L-form configuration that is intended unless the D-form is expressly designated. An alkyl group, if not specified, contains 1–12 carbon atoms.

The peptide of the invention can be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or pamoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition will depend on the peptide used. The peptide typically will be present in the composition in an amount from about 0.001% to about 10% by weight, in particular in an amount from about 0.005% to about 5% by weight.

The method for synthesizing peptides of the present invention are well documented and are within the ability of a person of ordinary skill in the art.

Topical Compositions

The topical compositions useful in the present invention involve formulations suitable for topical application to the skin or hair. In one embodiment, the composition contains a safe and effective amount of (i) at least one compound selected from the group consisting of copper PCA and an ester thereof, (ii) at least one compound selected from the group consisting of tyrosine and DOPA, and a salt or ester thereof, and (iii) a cosmetically-acceptable topical carrier. In one embodiment, the cosmetically-acceptable topical carrier is from about 50% to abut 99.99%, by weight, of the composition (e.g., from about 80% to about 99%, by weight, of the composition.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, nail lacquers, wound dressing and adhesive bandages, hydrogels, film-forming products, facial masks and skin masks, films and make-up such as foundations, mascaras, and lipsticks. These product types may contain several types of cosmetically-acceptable topical carriers including, but not limited to solutions, suspensions, emulsions such as microemulsions and nanoemulsions, gels, solids and liposomes. The following are non-limitative examples of such carriers. Other carriers can be formulated by those of ordinary skill in the art.

The topical compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, and mixtures thereof.

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656–61, 1626, and 1654–55 (The Cosmetic, Toiletry, and Fragrance Assoc., Washington, D.C., 7$^{th}$ Edition, 1997) (hereinafter "ICI Handbook").

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The topical compositions of the present invention may also be anhydrous compositions containing no water but organic and/or silicone solvents, oils, lipids and waxes.

Yet another type of product that may be formulated from a solution is an ointment. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 1693–1697.

The topical compositions useful in the present invention formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp.1673–1686.

Lotions and creams can be formulated as emulsions. Typically such lotions contain from 0.5% to about 5% of an emulsifier(s). Such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. In one embodiment, the copper PCA and/or ester thereof, tyrosine and/or DOPA and/or a salt or ester thereof, dihydroxyacetone, lawsone, pigment, and/or peptide are contained within the liposome. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water. Epidermal lipids of suitable composition for forming liposomes may be substituted for the phospholipid. The liposome preparation may then incorporated into one of the above carriers (e.g., a gel or an oil-in-water emulsion) in order to produce the liposomal formulation.

In one-embodiment, the liposome is non-ionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome contains glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical composition in an amount, based upon the total volume of the composition, of from about 5 mg/ml to about 100 mg/ml such as from about 10 mg/ml to about 50 mg/ml. Methods of preparing liposomes are well known in the art, such as those disclosed in U.S. Pat. No. 5,013,497 and 5,260,065.

Micelle formulations are also useful compositions of the present inventions. Such micelle compositions are disclosed in the U.S. Pat. No. 6,284,234.

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further contains another cosmetically active agent in addition to the copper PCA and/or ester thereof and tyrosine, DOPA, and/or a salt or ester thereof. What is meant by a "cosmetically active agent" is a compound (e.g., a synthetic compound or a compound isolated from a natural source) that has a cosmetic or therapeutic effect on the skin, hair, or nails, including, but not limiting to, lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in PCT Patent Application No. WO 00/15188, amino acids such a proline, vitamins, lactobionic acid, acetyl-coenzyme A, niacin, riboflavin, thiamin, ribose, electron transporters such as NADH and FADH2, and other botanical extracts such as aloe vera, and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid. See, e.g., European Patent Application No. 273,202.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Other Materials

Various other materials may also be present in the compositions useful in the subject invention. These include humectants, proteins and polypeptides, preservatives and an alkaline agent. Examples of such agents are disclosed in the ICI Handbook, pp.1650–1667. The compositions of the present invention may also contain chelating agents (e.g., EDTA) and preservatives (e.g., parabens). Examples of suitable preservatives and chelating agents are listed in pp.

1626 and 1654–55 of the ICI Handbook. In addition, the topical compositions useful herein can contain conventional cosmetic adjuvants, such as dyes, opacifiers (e.g., titanium dioxide), pigments, and fragrances.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

The composition and formulations containing such compositions of the present invention may be prepared using methodology that is well known by an artisan of ordinary skill.

EXAMPLE 1

Rhubarb Induces Pigmentation in Pigmented Epidermal Equivalents

Rhubarb was tested for its ability to induce pigmentation in pigmented epidermal equivalents. The Rhubarb extract was a powder obtained from an aqueous extract from the plant's root (JiangYing TianJiang Pharmaceutical, Inc., China). The extract was dissolved in PBS and tested for its ability to induce pigmentation in pigmented epidermal equivalents. The pigmented epidermal equivalents contained human normal melanocytes, together with normal, human-derived epidermal keratinocytes, which have been cultured to form a multi-layered, highly differentiated model of the human epidermis. Type II and IV pigmented epidermal equivalents (consisting of normal human keratinocytes pooled from variety of phototype skins and normal human melanocytes derived from type II or IV phototype skin) were treated with test compounds for three or five days and samples were harvested on the fourth or sixth day of the study. The harvested equivalents were stained with DOPA (a substrate for tyrosinase) or with Fontana-Mason (F&M) (Sheenan D C, Hrapckak B B, eds: Theory and practice of Histo-Thchnology (St Louis: C V Mosby, 1980) pp 223–277). F&M staining identifies silver nitrate reducing activity, which, in skin, identifies melanin.

The epidermal equivalents used were SkinEthic® reconstructed human epidermis from SkinEthic™ Laboratory (Nice, France). UV irradiation was performed with a UVB FS light source in an exposure chamber, with plate covers removed and Phosphate-buffered saline (PBS, from Gibco-BRL, Gaithersburg, Md.) present in the lower chamber. UVB intensity was measured with a UVX radiometer (UVP Inc., San Gabriel, Calif.). Equivalents were treated with 0.1–0.12 J/cm2. No loss of viability was observed in equivalents treated with up to 0.3 J/cm2. Rhubarb extract was assayed at 0.1–1 (w/v) concentration and was dissolved in PBS.

On the fourth or sixth day of the study, the equivalents were fixed, sectioned and F&M stained, or they were DOPA stained as whole without sectioning, using standard techniques. At least three sections per equivalent, three equivalents per experiment were processed. Each experiment was repeated three times. DOPA-stained epidermal equivalents were evaluated for the change in tyrosinase activity. F&M-stained histological sections were evaluated for the change in pigment deposition. The pigment change was evaluated using the scale defined in Table 1.

TABLE 1

| Score | Description |
|---|---|
| 0 | No change in DOPA staining and in melanin deposition |
| 1 | Minimal increase in DOPA staining and/or in pigment deposition |
| 2 | Increased DOPA staining and/or in pigment deposition |
| 3 | Strong increase in DOPA staining and/or in pigment deposition |

Table 2 represents the overall score in change of pigmentation, as evaluated by DOPA and F&M staining, as set forth above, when equivalents were exposed to Rhubarb (0.1%–1% (w/v)), OR UVB irradiation (0.10 J/cm$^2$). This table demonstrates that Rhubarb treatment resulted in darkening levels similar to those produced by UVB irradiation. In addition, Rhubarb treatment increased dendricity of melanocytes, suggesting that it may increase the transferring of melanosomes from melanocytes into keratinocytes.

TABLE 2

| | Score | | |
|---|---|---|---|
| Test Material | DOPA staining (tyrosinase activity) | F&M staining (Pigment deposition) | Overall Score |
| Control | 0 | 0 | 0 |
| UVB (positive control) | 3 | 2–3 | 2–3 |
| Rhubarb 0.1% | 2–3 | 1–2 | 1–2 |
| Rhubarb 0.5% | 2–3 | 2–3* | 2–3 |
| Rhubarb 1% | 2–3 | 3* | 2–3 |

*with a significant increase of melanocyte dendricity in the skin equivalents.

EXAMPLE 2

Rhubarb Induces Pigmentation In Vivo

Dark skinned Yucatan microswine (Charles River, Portland, Me.) were housed in appropriately sized cages in an environmentally controlled room with a 12-hour light—12-hour dark photoperiod and supplied with food and water ad libitum. Twenty $\mu$l of test materials were applied topically, twice a day, five days/week, for eight or nine weeks, on the dorsum of the swine. Treatments of individual swine were always arranged in a head to tail order on one side, and in a tail to head order on the other side of the animal. Biopsies were taken using standard techniques. All swine studies presented here had no visual irritation, and histological analyses revealed no markers of irritation or other pathological signs.

Swine were treated with either 1–5% (w/v) of the same rhubarb extract of Example 1 or ultraviolet-B radiation (as a positive control). The rhubarb extract was dissolved in ethanol: propylene glycol 70:30 (v/v). A mean erythema dose (MED) of UVB was determined by placing a plastic template with 1×1 inch$^2$ cutouts on the dorsum of the swine. Using a UVB lamp (Model UVM-57, 302 nm lamp, UVP Inc., Upland, Calif.) placed on the template, sites were exposed to UVB with increasing time points, every other day for five days. Unexposed sites were covered with the same material as the template. One MED was established as the dose that produces the least amount of visible erythema.

Swine were exposed to one MED, once per day, on three alternate days (Mon, Wed, Fri).

Following eight weeks of treatment, skin biopsies were taken using standard methods, for pigment deposition analysis. Sections from the skin biopsies were stained with Hematoxylin and Eosin (H&E), or with Fontana-Mason (F&M), using standard procedures (Sheenan DC, Hrapckak BB, eds., Theory and Practice of Histo-Technology (The C. V. Mosby Co., St. Louis (1980) pp. 223–277). At least three sections per biopsy were processed. Each experiment was repeated at least two times.

Histological analysis revealed an increase in pigment deposition in swine treated with rhubarb. Criteria for evaluation were total increase in pigment deposition, and the presence of capped epidermal cells above the basal layer. Table 4 represents the average value of all sites of responsive swine treated with each test material. The scale for evaluation is defined in Table 3.

TABLE 3

| Score | Description |
| --- | --- |
| −1 | Slight lightening |
| 0 | No change |
| 1 | Minimal increase in pigment deposition |
| 2 | Increased pigment deposition |
| 3 | Strong increase in pigment deposition, some increase in caps |
| 4 | Strong increase in pigment deposition, strong increase in caps |

TABLE 4

| Compositions | Score |
| --- | --- |
| Control | 0 |
| Ethanol: polypropylene glycol | 0 |
| UVB | 4 |
| 1% (w/v) rhubarb | 1–3 |
| 5% (w/v) rhubarb | 2–3 |

This example demonstrates that rhubarb enhanced pigment deposition in, and thereby darkened, live skin.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of darkening the skin, said method comprising topically applying to the skin a composition comprising a safe and effective amount of a rhubarb extract.

2. A method of claim 1, wherein said composition further comprises at least one pigment.

3. A method of claim 2, wherein at least one of said at least one pigment is melanin, a derivative of melanin, $CuCl_2$, Hedychium extract, or Bearberry extract.

4. A method of claim 1, wherein said composition further comprises dihydroxyacetone.

5. A method of claim 1, wherein said composition comprises from about 0.001%, by weight, to about 20%, by weight, of said rhubarb extract.

6. A method of claim 2, wherein said composition comprises from about 0.001%, by weight, to about 20%, by weight, of said rhubarb extract and from about 0.001%, by weight, to about 20%, by weight, of said at least one pigment.

7. A method of claim 3, wherein said composition comprises from about 0.001%, by weight, to about 20%, by weight, of said rhubarb extract and from about 0.001%, by weight, to about 20%, by weight, of said at least one pigment.

8. A method of claim 4, wherein said composition comprises from about 0.001%, by weight, to about 20%, by weight, of said rhubarb extract, from about 0.001%, by weight, to about 10%, by weight, of said dihydroxyacetone.

9. A method of darkening the hair, said method comprising topically applying to the hair a composition comprising a safe and effective amount of a rhubarb extract.

10. A method of claim 9, wherein said composition further comprises at least one pigment.

11. A method of claim 10, wherein at least one of said at least one pigment is melanin, a derivative of melanin, $CuCl_2$, Hedychium extract, or Bearberry extract.

12. A method of claim 9, wherein said composition comprises from about 0.001%, by weight, to about 20%, by weight, of said rhubarb extract.

13. A method of claim 10, wherein said composition comprises from about 0.001%, by weight, to about 20%, by weight, of said rhubarb extract and from about 0.001%, by weight, to about 20%, by weight, of said at least one pigment.

14. A method of claim 11, wherein said composition comprises from about 0.001%, by weight, to about 20%, by weight, of said rhubarb extract and from about 0.001%, by weight, to about 20%, by weight, of said at least one pigment.

* * * * *

SEQUENCE LISTING

```
<160> NUMBER OF SEQ ID NOS: 30

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: C-terminal amidation
<220> FEATURE:
<221> NAME/KEY: MISC_FEATURE
<222> LOCATION: (4)..(4)
<223> OTHER INFORMATION: C-terminal Amidation

<400> SEQUENCE: 1

Leu Ile Gly Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: C-terminal Amidation

<400> SEQUENCE: 2

Leu Ile Gly Arg Leu
1               5
```

```
<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: C-terminal Amidation

<400> SEQUENCE: 3

Leu Ile Gly Lys
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: C-terminal Amidation

<400> SEQUENCE: 4

Ser Leu Ile Gly Lys
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Leu Ile Gly Arg
1

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

Leu Ile Gly Arg Leu
1               5

<210> SEQ ID NO 7
<211> LENGTH: 4
<212> TYPE: PRT
<213> ORGANISM: Artificial Sequence
<220> FEATURE:
<223> OTHER INFORMATION: Sythetetic Peptide

<400> SEQUENCE: 7

Leu Ile Gly Lys
1

<210> SEQ ID NO 8
<211> LENGTH: 5
<212> TYPE: PRT
<213> ORGANISM: Artificial Sequence
```

```
<220> FEATURE:
<223> OTHER INFORMATION: Synthetic Peptide

<400> SEQUENCE: 8

Ser Leu Ile Gly Lys
1               5

<210> SEQ ID NO 9
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 9

Leu Ile Gly Arg
1

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (5)..(5)
<223> OTHER INFORMATION: Amidated C-terminus

<400> SEQUENCE: 10

Leu Ile Gly Arg Leu
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 11

Leu Ile Gly Lys
1

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: Palmitoyl N-terminus
<220> FEATURE:
<221> NAME/KEY: MISC_FEATURE
<222> LOCATION: (5)..(5)
<223> OTHER INFORMATION: Amidated C-terminus

<400> SEQUENCE: 12

Ser Leu Ile Gly Lys
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 13

Leu Ile Gly Arg
1

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 14

Leu Ile Gly Arg Leu
1               5

<210> SEQ ID NO 15
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 15

Leu Ile Gly Lys
1

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Palmitoyl N-terminus

<400> SEQUENCE: 16

Ser Leu Ile Gly Lys
```

```
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 17

Leu Ile Gly Arg
1

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (5)..(5)
<223> OTHER INFORMATION: Amidated C-terminus

<400> SEQUENCE: 18

Leu Ile Gly Arg Leu
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (4)..(4)
<223> OTHER INFORMATION: Amidated C-terminus

<400> SEQUENCE: 19

Leu Ile Gly Lys
1

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus
<220> FEATURE:
<221> NAME/KEY: MISC_FEATURE
<222> LOCATION: (5)..(5)
```

```
<223> OTHER INFORMATION: Stearatoyl C-terminus

<400> SEQUENCE: 20

Ser Leu Ile Gly Lys
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus

<400> SEQUENCE: 21

Leu Ile Gly Arg
1

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus

<400> SEQUENCE: 22

Leu Ile Gly Arg Leu
1               5

<210> SEQ ID NO 23
<211> LENGTH: 4
<212> TYPE: PRT
<213> ORGANISM: Artificial Sequence
<220> FEATURE:
<223> OTHER INFORMATION: Sythetic Peptide
<220> FEATURE:
<221> NAME/KEY: MISC_FEATURE
<222> LOCATION: (11)..(1)
<223> OTHER INFORMATION: Stearatoyl N-terminus

<400> SEQUENCE: 23

Leu Ile Gly Lys
1

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Stearatoyl N-terminus

<400> SEQUENCE: 24

Ser Leu Ile Gly Lys
1               5

<210> SEQ ID NO 25
<211> LENGTH: 6
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Amidated C-terminus

<400> SEQUENCE: 25

Ser Leu Ile Gly Arg Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 26

Ser Leu Ile Gly Arg Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Amidated C-terminus
<220> FEATURE:
<221> NAME/KEY: MISC_FEATURE
<223> OTHER INFORMATION: Palmitoyl N-terminus

<400> SEQUENCE: 27

Ser Leu Ile Gly Arg Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Palmitoyl N-terminus

<400> SEQUENCE: 28

Ser Leu Ile Gly Arg Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Amidated C-terminus
<220> FEATURE:
<221> NAME/KEY: MISC_FEATURE
<223> OTHER INFORMATION: Stearatoyl N-terminus

<400> SEQUENCE: 29

Ser Leu Ile Gly Arg Leu
1               5
```

```
<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Stearatoyl N-terminus

<400> SEQUENCE: 30

Ser Leu Ile Gly Arg Leu
1               5
```